(12) United States Patent
Nowazyk

(10) Patent No.: US 9,213,216 B2
(45) Date of Patent: Dec. 15, 2015

(54) LOW NOISE PHOTO-PARAMETRIC SOLID STATE AMPLIFIER

(71) Applicant: THE BRAIN WINDOW, INC., Los Angeles, CA (US)

(72) Inventor: Andreas G. Nowazyk, Los Angeles, CA (US)

(73) Assignee: The Brain Window, Inc., Los Angeles, CA (US)

( * ) Notice: Subject to any disclaimer, the term of this patent is extended or adjusted under 35 U.S.C. 154(b) by 0 days.

(21) Appl. No.: 14/506,278

(22) Filed: Oct. 3, 2014

(65) Prior Publication Data

US 2015/0138629 A1   May 21, 2015

Related U.S. Application Data

(62) Division of application No. 13/298,066, filed on Nov. 16, 2011, now Pat. No. 8,901,997.

(51) Int. Cl.

| | |
|---|---|
| *H03F 3/08* | (2006.01) |
| *H03F 7/00* | (2006.01) |
| *G02F 1/39* | (2006.01) |
| *G01N 21/27* | (2006.01) |
| *G01N 21/64* | (2006.01) |
| *G02B 21/00* | (2006.01) |
| *G01J 3/02* | (2006.01) |
| *G01J 3/10* | (2006.01) |

(52) U.S. Cl.
CPC *G02F 1/39* (2013.01); *G01N 21/27* (2013.01); *G01N 21/64* (2013.01); *G01N 21/645* (2013.01); *G02B 21/0096* (2013.01); *H03F 3/08* (2013.01); *H03F 7/00* (2013.01); *G01J 3/0264* (2013.01); *G01J 3/108* (2013.01); *G01N 2201/123* (2013.01); *G02F 2001/392* (2013.01)

(58) Field of Classification Search
CPC ..... G02F 1/39; G02F 2001/392; G01N 21/27; G01N 21/64; G01N 21/645; H03F 3/08; H03F 7/00
See application file for complete search history.

(56) References Cited

U.S. PATENT DOCUMENTS

| | | |
|---|---|---|
| 3,280,336 A | 10/1966 | Roulston |
| 3,378,640 A | 4/1968 | Sabban et al. |
| 3,391,346 A | 7/1968 | Uhlir, Jr. |
| 3,448,220 A | 6/1969 | Schlichte |
| 3,484,698 A | 12/1969 | Ruppli |
| 3,659,122 A | 4/1972 | Kaliski |
| 3,660,673 A | 5/1972 | Anderson |
| 3,679,985 A | 7/1972 | Fang et al. |
| 3,699,454 A | 10/1972 | Hudspeth et al. |
| 3,710,268 A | 1/1973 | Neuf |
| 3,831,038 A | 8/1974 | Dabby et al. |
| 3,875,422 A | 4/1975 | Stolen |
| 4,233,530 A | 11/1980 | Mikoshiba et al. |
| 4,365,216 A | 12/1982 | Minagawa et al. |

(Continued)

FOREIGN PATENT DOCUMENTS

JP          10209974 A  *  8/1998   ............ H04B 10/28

*Primary Examiner* — Eric Bolda
(74) *Attorney, Agent, or Firm* — Arent Fox LLP

(57) ABSTRACT

A solid state detection system includes a degenerate photo-parametric amplifier (PPA), wherein the PPA comprises a photo diode, and a periodically pulsed light source, wherein the photo-parametric, amplifier (PPA) is synchronized to the pulsed light source with a phase locked loop that generates a pump waveform for the PPA at twice the frequency of the excitation pulse rate.

20 Claims, 2 Drawing Sheets

(56) References Cited

U.S. PATENT DOCUMENTS

| | | | |
|---|---|---|---|
| 4,426,737 A | | 1/1984 | Mori |
| 4,638,257 A | | 1/1987 | McDonald |
| 5,481,104 A | * | 1/1996 | Miller et al. ............ 250/214 C |
| 5,751,747 A | | 5/1998 | Lutes et al. |
| 7,394,592 B2 | | 7/2008 | Fox et al. |
| 7,843,283 B2 | | 11/2010 | Reichenbach et al. |
| 8,175,126 B2 | | 5/2012 | Rakuljic et al. |
| 8,483,581 B2 | | 7/2013 | Suzuki |
| 8,659,814 B2 | | 2/2014 | Matsko et al. |
| 2004/0197234 A1 | * | 10/2004 | Endo et al. ............ 422/82.11 |
| 2005/0270091 A1 | | 12/2005 | Kozyrev et al. |
| 2013/0207725 A1 | | 8/2013 | Afshari et al. |

\* cited by examiner

LOW NOISE PHOTO-PARAMETRIC SOLID STATE AMPLIFIER

CROSS-REFERENCE TO RELATED APPLICATIONS

This application is a division of U.S. patent application Ser. No. 13/298,066, entitled "LOW NOISE PHOTO-PARAMETRIC SOLID STATE AMPLIFIER," filed Nov. 16, 2011 which is incorporated by reference herein.

BACKGROUND

1. Field

The present disclosure relates to optical amplification, and particularly relates to a photo-parametric amplifier that uses the properties of solid state detectors for very low noise amplification of weak, pulsed, high frequency optical signals.

2. Description of Related Art

Many biomedical instruments require the detection of very faint optical signals. For example the fluorescence of a single dye molecule that is coupled to an antibody may yield information about where a particular protein is located within a cell, but it produces very few photons/sec even with strong illumination. Many instruments detect such weak light sources with photomultiplier tubes (PMTs), where a photocathode converts a photon into a free electron, which is then accelerated by an electrical field to a dynode. Typical PMTs use 10 dynodes and provide a current amplification by a factor of about one million.

The internal gain is the significant advantage for PMTs over solid state photo detectors which have no built-in gain mechanism and which have to rely on external electronics to amplify the photo current to usable levels. PMT optical amplifiers outperform those based on photodiodes (solid state photodetectors) in terms of overall sensitivity and signal to noise ratio, even though photodiodes are actually much better at sensing light. The quantum efficiency (i.e., the probability for one photon to generate one electron) of a photodiode often exceeds 80% while it is rare that PMT has a quantum efficiency that approaches 30%.

Photodiodes are extremely linear devices, the current output is strictly proportional to the light input for over 12 decades while a PMT barely maintains linearity over 3 decades. Photodiodes are very rugged devices that are not harmed by exposure to high light levels, while PMTs are fragile and easily destroyed by exposure to room light levels while powered on. Photodiodes are available that operate well with IR light, while PMTs can barely detect light in the near IR spectrum. Photons with wavelength in excess of 1 micrometer do not have enough energy to free an electron, thus there are no practical PMTs that can cover the 1-2 micrometer wavelength range, while solid state detectors exist that can operate up to 10 micrometer wavelengths. Finally, PMTs are large, fragile, expensive and require high voltages to operate while solid state detectors are small, rugged and relatively inexpensive. In summary, the photo diodes outperform PMTs in most aspects other than built-in amplification by a wide margin.

SUMMARY

In an aspect of the disclosure, a solid state detection system includes a degenerate photo-parametric amplifier (PPA), wherein the PPA comprises a photo diode, and a periodically pulsed light source, wherein the photo-parametric amplifier (PPA) is synchronized to the pulsed light source with a phase locked loop that generates it pump waveform for the PPA at twice the frequency of the excitation pulse rate.

In an aspect of the disclosure, a photo-parametric amplifier (PPA) includes an input port to receive a pump input signal; a first LC resonant circuit coupled to the input port; a photodiode having an anode coupled to the first LC resonant circuit; a second LC resonant circuit coupled to a cathode of the photodiode; and an output port coupled to the second LC resonant circuit.

In an aspect of the disclosure, a microscope for imaging includes an optical system; a periodically pulsed light source configured to provide light to the optical system, wherein the photo-parametric amplifier (PPA) is synchronized to the pulsed light source with a phase locked loop that generates a pump waveform for the PPA twice the frequency of the excitation pulse rate; and a degenerate photo-parametric amplifier (PPA) configured to receive light output from the optical system, wherein the PPA comprises a photodiode.

DETAILED DESCRIPTION

Figure 1:
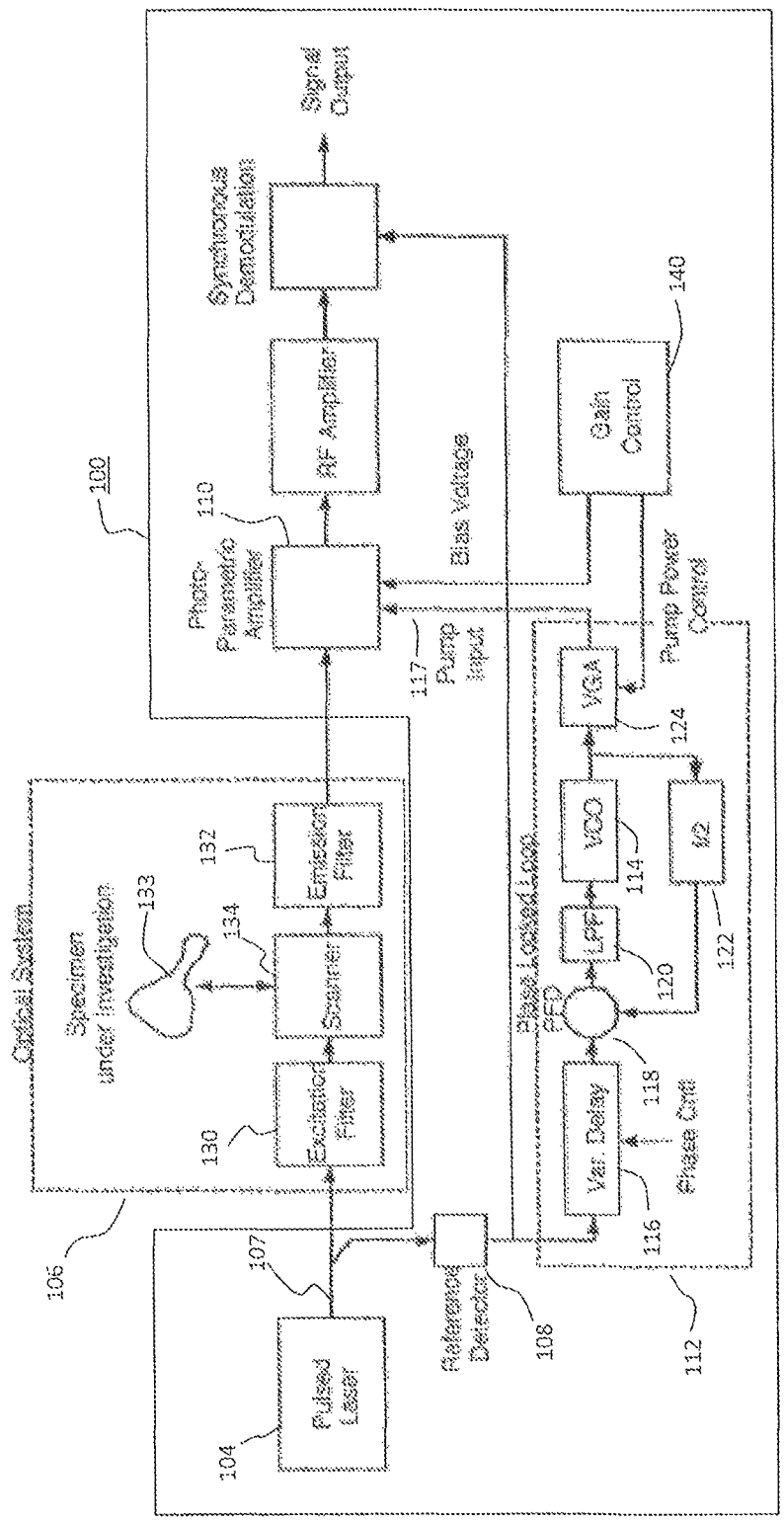
FIG. 1 is a conceptual representation of an aspect of a system for photo-parametric amplifier (PPA) sensing and/or imaging in accordance with the disclosure.

Various aspects of the present invention will be described herein with reference to drawings that are schematic illustrations of idealized configurations of the present invention. As such, variations from the shapes of the illustrations as a result, for example, manufacturing techniques and/or tolerances, are to be expected. Thus, the various aspects of the present invention presented throughout this disclosure should not be construed as limited to the particular shapes of elements (e.g., regions, layers, sections, substrates, etc.) illustrated and described herein but are to include deviations in shapes that result, for example, from manufacturing. By way of example, an element illustrated or described as a rectangle may have rounded or curved features and/or a gradient concentration at its edges rather than a discrete change from one element to another. Thus, the elements illustrated in the drawings are schematic in nature and their shapes are not intended to illustrate the precise shape of an element and are not intended to limit the scope of the present invention.

It will be understood that when an element such as a region, layer, section, substrate, or the like, is referred to as being "on" another element, it can be directly on the other element or intervening elements may also be present. In contrast, when an element is referred to as being "directly on" another element, there are no intervening elements present, it will he farther understood that when an element is referred to as being "formed" on another element, it can be grown, deposited, etched attached, connected, coupled, or otherwise prepared or fabricated on the other element or an intervening element. In addition, when a first element is "coupled" to a second element, the first element may be directly connected to the second element or the first element may he indirectly connected to the second element with intervening elements between the first and second elements.

Furthermore, relative terms, such as "lower" or "bottom" and "upper" or "top," may be used herein to describe one element's relationship to another element as illustrated in the drawings. It will be understood that relative terms are intended to encompass different orientations of an apparatus in addition to the orientation depicted in the drawings. By way of example, if an apparatus in the drawings is turned over, elements described as being on the "lower" side of other elements would then be oriented on the "upper" side of the other elements. The term "lower" can therefore encompass both an orientation of "lower" and "upper," depending of the particular orientation of the apparatus. Similarly, if an apparatus in the drawing is turned over, elements described as "below" or "beneath" other elements would then be oriented "above" the other elements. The terms "below" or "beneath" can therefore encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure.

As used herein, the singular forms "a," "an," and "the" are intended to include the plural forms as well, unless the context clearly indicates otherwise. It will be further understood that the terms "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

A structure and method is disclosed using photo-parametric amplification (PPA) to detect light in biomedical applications that use pulsed lasers for excitation.

FIG. 1 is a conceptual representation of a system 100 for PPA sensing and/or imaging. Light 107 originates from a pulsed laser 104 and is directed mostly to an optical system 106. A small fraction of the laser output 107 is diverted to a reference detector 108 that is used to synchronize a photo-parametric amplifier 110 to the laser 104. The reference signal is amplified by the reference detector and fed to a phase locked-loop circuit 112 that controls a voltage controlled frequency oscillator (VCO) 114 optimized for low phase noise and high spectral purity. It is understood that the noise of this VCO 114 may be limit the performance of the photo-parametric amplifier 110, hence a high quality VCO 114 is desirable. The phase locked loop (PH) circuit 112 includes a variable delay mechanism 116 to adjust the phase of a pump signal 117 with respect to the laser output 107. The PLL circuit 112 includes a phase frequency detector (PFD) 118, a low pass filter (LPF) 120, the VCO 114 and a frequency divider (f/2) 122. Typically, this functionality may be integrated into one commercially available integrated circuit.

The laser light 107 may be passed through various optical filters (excitation filter 130 and/or filter 132) and is directed at a specimen 133 under investigation. By using a scanning mechanism 134, scanned point sensing, may provide an image. The collected light from the specimen 133 under investigation is directed to the photo-parametric amplifier 110, where it may first pass through the emission filter 132, where the emission filter may include one or more spectrometers (not shown). As an example, in biomedical applications, the sensed light is not the light that was used to illuminate the specimen 133. Rather, processes such as fluorescence, second harmonic generation, and Raman scattering may used to measure molecular properties of the specimen 133. The most common of these methods is the use of fluorescence from certain dye molecules that are attached to antibodies which in turn selectively bind to specific proteins, e.g., at specific sites. Thus the fluorescence light reports the location of the protein of interest. For this invention to be applicable to such indirect imaging methods, it is preferable that the periodic modulation of the excitation signal is preserved by the imaging process and is present in the emission signal. This is the case for the non-linear processes such as second-harmonic generation and Raman scattering. Furthermore, the fluorescent lifetime of most organic dyes is in the sub-10 nano-second range, which means that the fluorescent signal from these dyes also retains most of the time varying structure of the laser illumination source 104. This also means that the practice of functional staining or labeling with green fluorescent proteins (GFP) can yield a signal that maintains the repetition frequency of the light source.

It may be noted, however, that the details of the optical system 106, including the scanning mechanism 134 and the interaction of the excitation light 107 with the specimen 133 under investigation may be of secondary importance to the disclosed apparatus. They are mentioned to provide an example of a possible application. The key elements of the disclosed apparatus include the use of a periodically pulsed light source, such as the laser 104 and the photo-parametric amplifier PPA 110 that is synchronized to the repetition rate of the light source.

Figure 2:
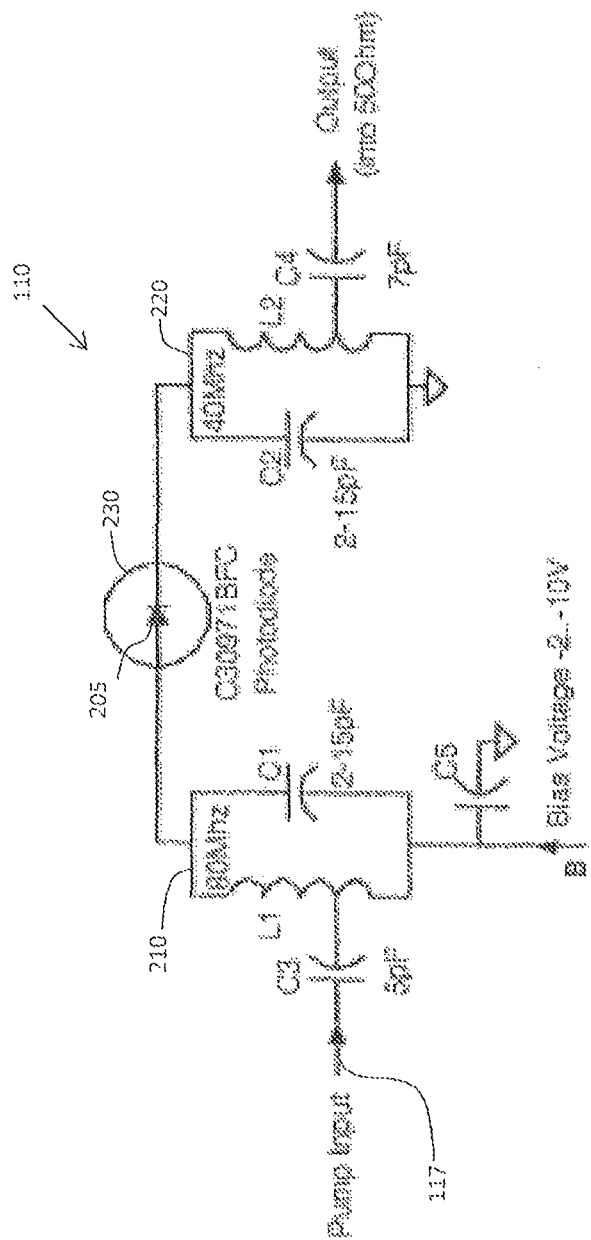
FIG. 2 is a conceptual representation of a photo-parametric amplifier circuit of FIG. 1.

An example of the photo-parametric amplifier 110 is depicted in the circuit in FIG. 2. As an example, the photo-parametric amplifier 110 was designed to operate at 40 MHz to match the repetition rate of a Fianium Supercontinuum laser [Fianium Ltd., 20 Compass Point, Ensign Way, Southampton SO31 4RA, United Kingdom], however, another amplifier speed may be designed to match another light source. In the example shown in FIG. 2, a light detector 205, such as a C30971BFC fast silicon photodiode from Perkin Elmer, may be integrated into a fiber-optic FC-type connector. It should be noted that this is a typical silicon photodiode and not a varactor diode specifically designed for microwave applications. Hence the diode is optimized for light sensitivity and not for its controllable junction capacitance. The photodiode 205 may be optimized for speed, which means that the internal series resistance is low, which in turn reduces its Johnson noise contribution. However, when the photodiode 205 is operated in the photo-conduction mode, that is with a reverse bias applied, its shot-noise dominates.

An inductor L1 and a capacitor C1 form a high-Q resonator 210 circuit that resonates at twice the frequency of the laser (e.g., 80 MHz, but variable and dependent on the laser), and which is excited from the pump input 117 via a capacitor C3. One or more capacitors that make up a capacitor C5 provide DC isolation of the pump-resonator 210 while blocking an RE signal path to ground. A connection B may be used to apply a reverse bias voltage (e.g., −2 to −10 V) to the photodiode 205 and also to measure the sum of a light induced DC photo-current and a dark current. The cathode of the photodiode is connected an inductor L2 and a capacitor C2, which form a LC-resonator 220 tuned to 40 Mhz. A case 230 of the photodiode 205 may preferably be grounded. The case 230 may be attached to RF-shielding (not shown) of the circuit. A signal from the resonator 220 may be coupled to the output of the PPA 110 via as capacitor C4. The entire PPA 110 may preferably be enclosed in an soldered RF-shield. The two tank circuits 210, 220 may preferably be located in separate shielded chambers and have very low inductive coupling.

Controlling gain is important for biomedical applications, and because of the high sensitivity of the gain to the pump power level, it is preferable that the PPA 110 include facilities to control and stabilize the power of the input pump 117. In one implementation, the output of the VCO 114 is fed to a variable gain amplifier (VGA) 124 which in turn drives the PPA 110. A fraction of the pump input 117 power is diverted to a stable sensor to measure the power delivered to the PPA 110. This value is compared to gain setting and the difference is used to adjust the gain of the VGA by a gain control 140. This is a form of open loop stabilization that relies on measuring the relation between PPA gain and pump power and that assumes that this calibration remains stable.

For some critical applications, closed loop stabilization may be preferable because of the high, sensitivity of the PPA gain to pump power and bias voltage. There are several methods that can be used to measure the PPA gain during operation: (a) Measure the shot-noise from the photo diode 205. The shot noise is proportional to the square-root of the sum of photo- and dark-current, which can be measured fairly easily. It has a broad spectral distribution that can be assumed to be uniform over the operating bandwidth. Thus, by measuring the signal strength of a narrow band just outside of the operating bandwidth and comparing that value to the expected noise for the actual photo diode current, a direct measure of the gain of tire entire amplification chain is achieved; (b) Add an optical pilot signal. For example by adding as fiber-optic link between the photo diode 205 and a reference light source. The reference light source can be a stabilized light emitting diode. The reference light source adds a very small signal at a frequency that is just outside of the operating bandwidth. This signal is subsequently detected at the output of the amplifier chain via synchronous demodulation and provides a direct measure of the total gain of the entire amplifier chain. While the extra light will add some noise to the system, it also provides a direct, stable end-to-end measure and permits long-term, reliable calibration of the instrument; (c) Add an electronic pilot signal. This method is identical to the method described above, except that it uses a loosely coupled probe to inject the pilot signal electronically into the resonant circuit of the PPA 110. This approach has the advantage that it does not add noise to the system. It also has the disadvantage that it does not include a measure of the conversion efficiency of the photodiode, which may change, depending on device age and temperature.

The gain of the PPA 110 also depends on the reverse bias of the photo diode 205. This bias voltage is essentially a mechanism to fine tune the PPA 110. The sensitivity of the PPA 110 on the bias voltage is modest; hence a digital to analog converter that produces 0-10V with 8 to 12 bits of resolution may be adequate. The PPA 110 performance can be optimized by changing the bias voltage depending on the pump-power level.

The overall sensitivity of the PPA 110 is limited by the dark current of the photodiode 205 and its associated shot noise in order to achieve the full potential of this light detection system, it may be preferable to cool the photo diode 205. Because the photodiode 205 generates no significant amount of heat, a conventional thermoelectric cooler may suffice.

The gain of a degenerate parametric amplifier, such as the PPA 110 described in this disclosure is phase sensitive, which means that it may be necessary to adjust the phase of the pump oscillator with respect to the excitation pulses. Controlling the phase of a phase locked loop, such as the one described above is easily done using any of a plurality of standard solutions for this type of problem, including electronic phase shifters, variable delay element or direct digital synthesis (DDS) in the PLL loop. For example an AD9540 integrated circuit from Analog Devices may be considered a suitable element for this purpose.

The fact that the PPA 110 is phase sensitive is beneficial for this application because out-of phase noise is attenuated, which effectively halves the noise contribution of this detection system (100). In addition, varying the phase of the detection system deliberately can be used as a sensing mechanism to measure the fluorescent lifetime of a molecule that is being sensed. The lifetime information can be used to discriminate between several signals with otherwise similar optical properties.

One of ordinary skill in the art will recognize that the system of imaging described herein is substantially more sensitive than conventional imaging.

The various aspects of this disclosure are provided to enable one of ordinary skill in the art to practice the present invention. Modifications to various aspects presented throughout this disclosure will be readily apparent to those skilled in the art, applications to other technical arts, and the concepts disclosed herein may be extended to such other applications. Thus, the claims are not intended to be limited to the various aspects photo-parametric amplification presented throughout this disclosure, but are to be accorded the full scope consistent with the language of the claims. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to he construed under the provisions of 35 U.S.C. §112, sixth paragraph, unless the element is expressly recited using the phrase "means for" or, in the ease of a method claim, the element is recited using the phrase "step for."

What is claimed is:

1. A photo-parametric amplifier (PPA), comprising:
   an input port configured to receive a pump input signal;
   a first LC resonant circuit coupled to the input port;
   a photodiode including an anode and a cathode, the anode of the photodiode coupled to the first LC resonant circuit;
   a second LC resonant circuit coupled to the cathode of the photodiode; and
   an output port coupled to the second LC resonant circuit.

2. The PPA of claim 1, further comprising a first capacitor, wherein the pump input signal is coupled to the first LC resonant circuit via the first capacitor.

3. The PPA of claim 1, wherein the photodiode is configured to receive a light signal at a selected excitation pulse rate from a periodically pulsed excitation light source.

4. The PPA of claim 1, wherein the first LC resonant circuit is coupled to a source of biasing voltage.

5. The PPA of claim 2, further comprising a second capacitor, wherein the first LC resonant circuit is coupled to a ground potential via the second capacitor in parallel with the source of biasing voltage.

6. The PPA of claim 2, wherein the first LC resonant circuit is coupled to the input port via the first capacitor.

7. The PPA of claim 3, wherein the first LC resonant circuit is configured to resonate at twice a frequency of a periodically pulsed excitation light source.

8. The PPA of claim 7, wherein the first LC resonant circuit is a high-Q resonator circuit.

9. The PPA of claim 5, wherein the second capacitor is configured to provide DC isolation of the first LC resonant circuit.

10. The PPA of claim 9, wherein the second capacitor is further configured to block a radio frequency (RF) signal path between the first LC resonant circuit and the ground potential.

11. The PPA of claim 10, further comprising a connector coupled to the second capacitor, wherein the connector is configured to apply a reverse bias to the photodiode.

12. The PPA of claim 11, wherein the connector is further configured to measure a DC photo-current and a dark current.

13. The PPA of claim 7, further comprising a third capacitor coupled to the second LC resonant circuit.

14. The PPA of claim 13, wherein the second LC resonant circuit is coupled to the output port via the third capacitor.

15. The PPA of claim 14, wherein the output port is configured to receive a signal from the second LC resonant circuit via the third capacitor.

16. The PPA of claim 1, further comprising a radio frequency (RF) shield.

17. The PPA of claim 1, further comprising a first housing, wherein the first LC resonant circuit is located in the first housing.

18. The PPA of claim 17, further comprising a second housing, wherein the second LC resonant circuit is located in the second housing.

19. The PPA of claim 18, wherein the first housing and the second housing are separate shielded chambers.

20. The PPA of claim 1, wherein the first LC resonant circuit is tuned to 80 MHz and the second LC resonant circuit is tuned to 40 MHz.

* * * * *